(12) United States Patent
Rosen et al.

(10) Patent No.: US 10,789,661 B2
(45) Date of Patent: Sep. 29, 2020

(54) COMPUTER SYSTEM AND COMPUTER IMPLEMENTED METHOD FOR REAL-TIME DRUG INTERACTION CHECKER

(71) Applicant: Express Scripts Strategic Development, Inc., St. Louis, MO (US)

(72) Inventors: Donna Rosen, Kinnelon, NJ (US); Tejwansh Anand, Chappaqua, NY (US); Yakov Esterlis, Cliffside Park, NJ (US); Eileen Bidell, Towaco, NJ (US); Keith Bradbury, Blauvelt, NY (US); Judith Heller, North Caldwell, NJ (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 76 days.

(21) Appl. No.: 16/015,877

(22) Filed: Jun. 22, 2018

(65) Prior Publication Data
US 2018/0374175 A1    Dec. 27, 2018

Related U.S. Application Data

(63) Continuation of application No. 13/299,330, filed on Nov. 17, 2011, now Pat. No. 10,026,137.

(60) Provisional application No. 61/414,670, filed on Nov. 17, 2010.

(51) Int. Cl.
G06Q 50/22    (2018.01)
G06Q 30/00    (2012.01)

(52) U.S. Cl.
CPC ............. *G06Q 50/22* (2013.01); *G06Q 30/00* (2013.01)

(58) Field of Classification Search
CPC ........ G06Q 50/22; G06Q 50/24; G06Q 30/00; G06Q 30/06; G16H 10/65; G06F 19/3456; G06F 19/328
USPC ........................................................ 705/2, 3
See application file for complete search history.

(56) References Cited

U.S. PATENT DOCUMENTS

| | | |
|---|---|---|
| 5,487,384 A | 1/1996 | Lee |
| 5,743,250 A | 4/1998 | Gonda et al. |
| 5,758,095 A | 5/1998 | Albaum et al. |
| 5,845,255 A | 12/1998 | Mayaud |
| 6,014,631 A | 1/2000 | Teagarden et al. |
| 6,356,873 B1 | 3/2002 | Teagarden et al. |
| 6,694,298 B1 | 2/2004 | Teagarden et al. |
| 7,197,125 B1 * | 3/2007 | Prasad ................ H04L 41/0893 379/201.02 |
| 7,711,583 B2 | 5/2010 | Epstein et al. |
| 8,335,695 B2 | 12/2012 | Cedergreen |
| 8,478,611 B2 | 7/2013 | Epstein et al. |
| 2001/0056359 A1 | 12/2001 | Abreu |

(Continued)

OTHER PUBLICATIONS

McMullin, et al., Impact of Web-Based Clinical Information System on Cisapride Drug Interactions and Patient Safety, Arch Intern Med, vol. 159, pp. 2077-2082, Sep. 1999.

(Continued)

*Primary Examiner* — Aryan E Weisenfeld
*Assistant Examiner* — Alaaeldin M Elshaer
(74) *Attorney, Agent, or Firm* — Husch Blackwell LLP

(57) ABSTRACT

A computer system and computer implemented method for performing web-based drug interaction screening utilizing access a patient's prescription history stored in the pharmacy's prescription history or in the health plan's claim history.

15 Claims, 15 Drawing Sheets

Pre-Authenticated LTPA Token Delivery

After receiving the token, DrugStore can call Medco's services for additional information to fulfill the user's activity on the DrugStore.com site as required. The LTPA Token is required for each request (Set in a specific HTTP Header given in the implementation section)

(56) References Cited

U.S. PATENT DOCUMENTS

| | | | |
|---|---|---|---|
| 2002/0010595 A1 | 1/2002 | Kapp | |
| 2003/0144883 A1 | 7/2003 | Fagerholm et al. | |
| 2004/0019502 A1 | 1/2004 | Leaman et al. | |
| 2004/0073457 A1* | 4/2004 | Kalies | G06F 19/3456 705/2 |
| 2004/0220835 A1 | 11/2004 | Muchin et al. | |
| 2005/0252966 A1* | 11/2005 | Kulas | G06Q 30/06 235/383 |
| 2006/0247968 A1 | 11/2006 | Kadry | |
| 2006/0282528 A1* | 12/2006 | Madams | H04L 51/00 709/224 |
| 2007/0093935 A1 | 4/2007 | Fu | |
| 2009/0265381 A1* | 10/2009 | Canu | G16H 10/65 |

OTHER PUBLICATIONS

Koide, et al., Computerized reminders to monitor liver function to improve the use of etretinate, International Journal of Medical Informatics, vol. 57, pp. 11-19, Jan. 2000.

Tierney et al., Computer Predictions of Abnormal Test Results, JAMA, vol. 259, pp. 1194-1198, Feb. 26, 1988.

Gonzalez et al., Computer-Assisted Optimizatino of Aminophylline Therapy in the Emergency Department, Am. J. Emerg. Med., vol. 7, 395-401, 1989.

Wolf et al., Psychiatric Admissions due to Adverse Drug Reactions, Comprehensive Psychiatry, vol. 30, No. 6, 1989, pp. 534-545.

Hansen et al. Risk Factors for Drug-Induced Parkinsonism in Tardive Dyskinesia Patients, Journal of Clinical Psychiatry, vol. 49, No. 4, 1988, pp. 139-141.

Leslie et al., Shifting to Outpatient Care? Mental Health Care Use and Cost Under Private Insurance, Am J Psychiatry, vol. 156, No. 8, 1999, pp. 1250-1257.

Alberts et al., Molecular Biology of the Cell, Third Edition, Garland Publishing, pp. 1-20, 1994.

Dowd, et al., Nonsteroidal Antinflammatory Drug-Induced Gastroduodenal Injury in Children, Arthritis & Rheumatism, vol. 38, No. 9, Sep. 1995, pp. 1225-1231.

Suhr, et al., Drug-Induced Headache: Long-term results of stationary versus ambulatory withdrawal therapy, Cephalalgia, vol. 19, pp. 44-49, 1999.

Ben-Ami, et al., Drug-Induced Hypoglycemic Coma in 102 Diabetic Patients, Arch Intern Med, vol. 159, Feb. 8, 1999 pp. 281-284.

* cited by examiner

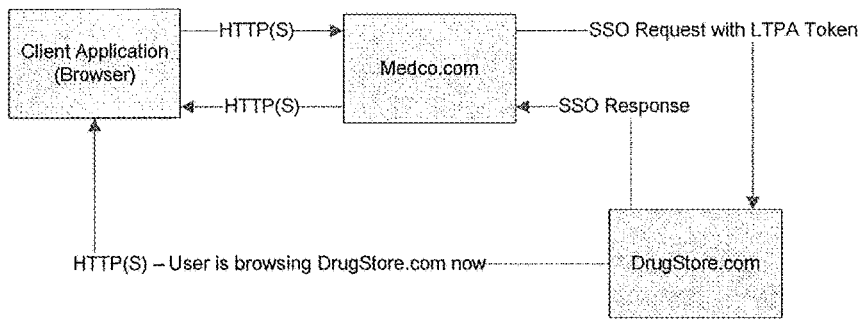

Pre-Authenticated LTPA Token Delivery

After receiving the token, DrugStore can call Medco's services for additional information to fulfill the user's activity on the DrugStore.com site as required. The LTPA Token is required for each request (Set in a specific HTTP Header given in the implementation section)

Fig. 1

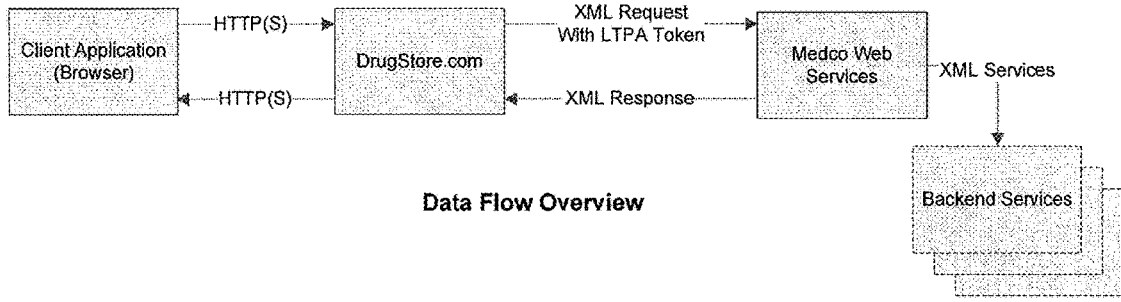

Data Flow Overview

Each successful request then renews the token and a new token is sent back, DrugStore must ensure that the new token is then used in all subsequent requests to prevent session timeout.

Fig. 2

Drug Interaction Checker Process
Step 1: Identify DUR-able items in the cart

- The DUR process is initiated only when a "DUR-able" item is in the cart
- First-time visitors with a DUR-able item in their cart will be routed to the Information Sharing Authorization approval page
- DUR will run automatically for returning visitors who have agreed to the Information Sharing Authorization
- DUR *only* runs for the individual logged in (not other members of the household)

| | Name | Qty. | Savings | Total |
|---|---|---|---|---|
| | Neutrogena Clean Shampoo Replenishing - 10.1 fl oz • see accessories for this product in stock | 1 remove | $.84 | $4.19 |
| | Q-tips Cotton Swabs - 1750 ea • see accessories for this product in stock | 1 remove | | $10.99 |
| | Advil Solubilized Ibuprofen Capsules, 200mg, Liquid Filled Capsules - 160 ea • see accessories for this product in stock | 1 remove | $4.00 | $14.99 |

Subtotal: $38.46
Total Savings: $4.84

Fig. 3

Drug Interaction Checker Process
DUR Step 2: Information Sharing Authorization

At Medco Health Store, your health is our top priority

Medco's Drug Interaction Checker helps ensure that the over-the-counter (OTC) purchases in your shopping bag will not have adverse effects when used with any of your prescription medications. In order to detect these adverse effects, Medco will need to share information about your prescription history with Medco Health Store.

Additionally, Medco Health Store may use this information to recommend products and services that may be particularly beneficial to you in managing your health. Please read the authorization below and select whether you agree to allow your prescription information to be shared in the manner described.

If you decide not to share your information with Medco Health Store, you will be taken straight to checkout.

Information Sharing Authorization

```
benefit manager, to disclose to Medco Health Store and for
Medco Health Store to use my prescription drug records to
check for known drug interactions with the over-the-counter
medicines that I am purchasing. I also authorize Medco Health
Store to use this information to recommend over-the-counter
```

Please make a copy and retain for your records using your browser's 'save' feature or click here to open a new window and use your browser's 'print' feature.

Selecting "I agree" below constitutes an electronic signature and authorizes the use and disclosure of my protected health information in the manner described above.

○ I agree to share my information with Medco Health Store
○ I do not agree to share my information with Medco Health Store

- ➤ The DUR process will only run for Members who agree to the Information Sharing Authorization

- ➤ Members may change the Information Sharing Preference on the My Account page

Fig. 4

Drug Interaction Checker Process
DUR Step 3: Determine product use

Drug Checker has analyzed your cart and needs more information

For each product shown below, please indicate whether the product is for your one-time use, ongoing user, or for use only by someone else. A record of products purchased for ongoing use will be stored in your Medco profile to use for future drug interaction checks. PLEASE NOTE: The drug checker runs against the prescription records of only the customer currently logged in - it does not check any other member of your household.

Please make a selection for each product below:

Bufferin Tri Buff Tab 130s - 100 Ea
Tablets, Coated Buffered Aspirin
in stock Please indicate if being purchased for:
- ⊙ My one-time use
- ○ My ongoing use
  What is the difference?
- ○ This product is only for someone else
  (Selecting this option will exclude this product from the drug interaction check)

▲ DUR identifies whether the product is for the member logged-in or someone else

▲ DUR identifies usage frequency

▲ OTC products indentified for ongoing use will be stored in the member profile and used in future DUR analysis

Fig. 5

Drug Interaction Checker Process
DUR Step 3: Determine product use

Drug Checker has analyzed your cart and needs more information

For each product shown below, please indicate whether the product is for your one-time use, ongoing else. A record of products purchased for ongoing use will be stored in your Medco profile to use for full NOTE: The drug checker runs against the prescription records of only the customer currently logged in of your household.

Please make a selection for each product below:

Bufferin Tri Buff Tab 130s - 100 Ea
Tablets, Coated Buffered Aspirin
in stock Please indicate i ○ My one-time use
○ My ongoing use
  <u>What is the difference?</u>
○ This product is only for someone else
  (Selecting this option will exclude this
  product from the drug interaction check)

The difference between one-time use and ongoing use

One-time use
One-time use indicates that the product is not routinely used as part of your health and wellness regimen. This type of product could be used for a condition that has a quick symptom onset and then subsides.

Ongoing use
Ongoing use indicates that you are taking the product on a regular basis. This type of product could be used for a condition or illness whose symptoms and signs last for a long time. A record of products purchased for ongoing use will be stored in your Medco profile to use for future drug interaction checks.

Fig. 6

Drug Interaction Checker Process
DUR Step 4: Results Page Messages (Yellow Notification Example)

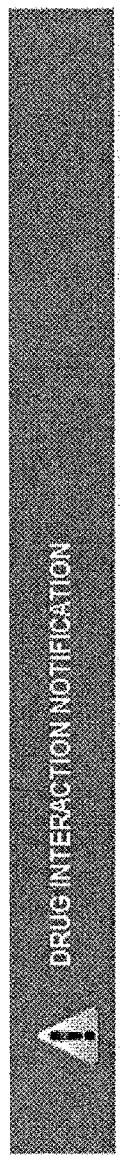

- An image of the OTC product is shown next to the potential interaction message
- 3 Possible Results:
  - No Potential Interactions
  - Yellow Notification
  - Red Warning
- Yellow Notifications are less severe than Red Alerts and directs the member to read the product label and discuss with a doctor or pharmacist before use

Fig. 8

Drug Interaction Checker Process
DUR Step 5: Continue to Checkout

Fig. 9

Drug Interaction Checker Process
Step 1: NO DUR-able items in the cart

Fig. 10

Drug Interaction Checker Process
Step 2: NO DUR-able items in Cart - Messaging

Fig. 11

UPC to NDC Product Mapper Service – Interaction Diagram

DURProductAlerts Service – Interaction Diagram

BUSINESS RULES
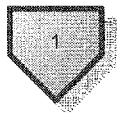 1. DUR consent only presented for "alert products"? HIPAA Consent for all OTCs?
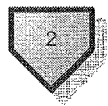 1. If DUR Consent, stored by drugstore and passed back to Medco with order data, DUR consent is required with each OTC purchase.
2. If HIPAA Auth, must be stored and managed by Medco.
 1. Hard alerts only for phase 1.
Fig. 16

COMPUTER SYSTEM AND COMPUTER IMPLEMENTED METHOD FOR REAL-TIME DRUG INTERACTION CHECKER

CROSS-REFERENCE TO RELATED APPLICATIONS

This application is a continuation of U.S. patent application Ser. No. 13/299,330, filed on Nov. 17, 2011; said application claims priority to U.S. Provisional Patent Application No. 61/414,670, filed Nov. 17, 2010, the entirety of said applications are hereby incorporated herewith.

FIELD OF THE INVENTION

The present invention generally relates to systems and methods for performing real-time checks for interactions of drugs, particularly the interactions between consumer products available without a prescription and current prescription medications.

BACKGROUND OF THE INVENTION

Generally, drug utilization review ("DUR"), on consumer purchases of non-prescription ("OTC"), products is not required or necessary on either the OTC purchasing side or the prescription dispensing side. There are a number of reasons including: (1) it is unclear who is actually using the OTC product, (2) most state laws require a "reasonable effort" to collect patient information (including OTC use); a DUR is not typically performed in the industry.

The growth and expansion of the internet and e-commerce has led to increased consumer purchases of OTC products from a computer rather than in a public setting with accessibility to a live pharmacist. When available in a public setting, a pharmacist can perform a review of the adequateness of an OTC product, and provide an alternative recommendation when a proposed OCT purchase would lead to a potential drug-drug or drug-disease interaction.

Accordingly, we have determined that there exists a need in the art for a computer system and computer implemented method to perform real-time drug interaction screening at the point of sale.

SUMMARY OF THE INVENTION

In some embodiments, the present invention may provide a solution to the lack of accessibility to the pharmacist when the consumer makes a web-based OTC purchase. In certain embodiments, "patient level" DUR is included (using combined RX and OTC product history), and that system and process will have the ability to identify who the individual patient for whom a particular purchase is made (i.e., the person with the household).

In certain embodiments, OTC purchase information may be placed on a patient's profile. This may be done at the patient level (i.e., we will know whether the OTC purchase is made for a particular individual). OTC information may be available to pharmacists with access to the patient's profile, and could be utilized in performing DUR when the pharmacist dispenses a prescription drug to the patient in the same manner DUR would be performed against (1) other prescription medications dispensed by the pharmacy, (2) prescription medications dispensed by another pharmacy within the pharmacy network, (3) self-reported prescription medications, (4) self-reported OTC products, and (5) diseases or chronic conditions.

In certain embodiments, a proposed OTC purchase is checked against a patient profile, a potentially serious interaction is identified, and an alternative OTC product is recommended.

In certain other embodiments, where the purchaser cannot be obtained, i.e., the purchaser may or may not be the patient. For OTC purchases, DUR would not be performed and the purchases would not be stored. In these transactions, the invention would provide a drug interaction checker tool for patients to perform their own DUR. In certain preferred embodiments, the drug interaction checker tool would have the capability to add OTC and/or prescription drugs one at a time. In certain more preferred embodiments, the user/patient interface would include a persistent link to the drug interaction checker tool throughout the site and independent from the purchase/order flows.

In certain other embodiments, where the purchaser cannot be obtained, i.e., the purchaser may or may not be the patient. For checking potential prescription purchases, the user interface would provide a drug interaction checker having the ability to add products one at a time.

In accordance with the above embodiments, the invention further provides a system and method where a family level addition listing all OTC purchases corresponding to a family can be checked.

In certain other embodiments of the present invention, the system and method will comprise DUR executed by a pharmacist specializing in a specific disease states selected from the group consisting of diabetes, cardiovascular disease, gastro-intestinal disorders, psychological/neurological conditions, hematology/oncology, and pulmonary conditions. In certain embodiments the invention allows for the ability for the user/purchaser to select products for the user or a member of the user's family that are included within the user's health plan. In certain preferred embodiments, the health plan comprises a drug benefit plan. In accordance with the above aspects of the invention, the process and system provides alerts to the user of potential drug-drug or drug-disease interactions. In certain preferred embodiments, the alerts are selected from the group consisting of severe drug-drug interactions, drug-drug interactions, drug-disease interactions, drug-disease interactions inferred by the patient's prescription history, and therapeutic duplication. In certain preferred embodiments, DUR leading to severe drug-drug interactions would not allow the user/purchase to complete the purchase of the OTC. In certain other preferred embodiments, DUR leading to a drug-drug interaction would allow the user/purchaser to complete the transaction while providing a warning of the interaction. In preferred aspects, patient information will be provided and/or the system will ensure clearly who the end/user patient is. In certain other embodiments, the user/purchaser will be provided the option of indicating the OTC is intended for household use and not for a particular patient.

In certain embodiments, OTC purchase information may be placed on a patient's profile and the user/purchaser will have the ability to indicate whether the prescription is for acute or chronic use. A skilled practitioner in the art would appreciate that this distinction is dependent on the particular product and the condition or symptom it is being used for. In certain preferred embodiments, acute refers to one time use and chronic refers to continuous or ongoing use. In certain embodiments, where the user/purchaser indicates that a product is for acute use, the system and process of the invention would provide a one-time snapshot DUR with user/purchaser acknowledgment. In certain other embodiments, the invention also provides the user/purchaser to add information into the user-initiated drug interaction checker including prescription history information and items selected for on-line purchase. In certain preferred embodiments, these are accomplished by buttons labeled 'load history' and 'add items in cart'.

In accordance with the above embodiments, where the user/purchaser indicates that a product is for chronic use, the system and process of the present invention would provide for a full DUR, the information on the OTC purchase would be saved in the patient profile and would be considered for future OTC and prescription dispenses. In certain preferred embodiments, these are accomplished by links labeled 'load history' and 'add items in cart'.

In accordance with the above embodiments, the system and process of the present invention would provide alerts of severe drug-drug interactions, drug-drug interactions and drug-disease interactions. In certain embodiments, the system and process would offer the ability to correct the patient if an incorrect patient was entered. In other embodiments where the alert is not severe, the user/purchaser would receive a message with a warning and permit the sale of the selected DUR message. In certain other embodiments, interactions are classified as severe interactions. One of skill in the art would appreciate that classification of severe is determined by clinical factors such as a more substantial likelihood of harm and/or a heightened severity of harm to the patient. In certain preferred embodiments where the message identifies a severe interaction, the system and method would not permit the completion of the selected OTC product. In certain other preferred embodiments of the present invention, the system and method would offer the user/purchaser to correct the patient information if incorrectly entered. In certain preferred embodiments, the messaging provides an option to speak with a specially trained pharmacist by dialing a phone number. In certain other embodiments the user/purchaser's phone call is received by an interactive voice response ("IVR"), system to navigate through inquiries with OTC product DUR inquires.

In accordance with the above embodiments, where the use of the OTC product is characterized as chronic use for the identified patient, the invention is further directed to systems and methods where OTC purchases are stored in a patient profile and considered during DUR by the pharmacy maintaining the profile or a pharmacy in the pharmacy network corresponding to the patient's health plan. In certain preferred embodiments, the OTC purchases are stored in the claims database of the patient's profile to enable DUR to consider these OTC products during subsequent transactions.

In accordance with the above embodiments, the invention further provides for systems and methods where the graphical user interface allows for access to the patient's prescription profile including a dispensing history while using the pharmacy associated With the health plan, e.g. prescription drug plan ("PDP"), and while using a pharmacy that submits claims for reimbursement to the PDP manager. In certain preferred embodiments, the graphical user interface provides one or more entry points into a platform that allows for shopping and purchase of OTC products. In certain other preferred embodiments, the platform is derived from a commercially available commerce platform, e.g., WebSphere Commerce, available from IBM Corp., Armonk, N.Y.

In accordance with the above embodiments, the invention provides warnings classified as major, moderate or minor. Major means the interaction may be life-threatening. In certain other embodiments, a major alert would direct the user/purchaser to call the patient's doctor immediately to discuss whether the patient should be taking the interacting medications together. Moderate means the interaction may make a condition worse. The patient's doctor may need to change the therapy. In certain other embodiments, a moderate alert would direct the user/purchaser to contact the patient's doctor or pharmacist about using the interacting products together. Minor means the interaction may increase the side effects of each drug. The patient can usually continue taking both drugs. In certain other embodiments, a minor alert would direct the user/purchaser to report any unusual or bothersome side effects to the patient's doctor.

In one aspect of the invention, the drug interaction checker system comprises one or more non-transitory computer storage media having stored thereon, computer executable instructions that, when executed, facilitate a process for determining drug interactions, the process comprising the following steps performed in sequential, non-sequential and sequence independent order: (i) identifying from a list of one or more OTC products selected for purchase during a shopping session utilizing an web-based commerce platform, products that could potentially interact with a prescription or OTC product of a patient, (ii) obtaining electronic authorization for the drug interaction checker to access information about the patient's prescription history, (iii) determining via responses to questions presented to the user/purchaser whether the patient will be using the one or more OTC products for one-time use or ongoing basis, (iv) comparing the combination of the one or more OTC products and the information available from the patient's prescription history against a list of possible drug interactions stored in a database, (v) identifying interactions and/or (vi) alerting the user the user/purchaser of those interactions.

In some embodiments of the invention, computer executable instructions further comprise a capability to: offer the user to change the initially identified patient to a second patient, obtain authorization to share prescription and health information with the drug interaction checker, and perform, for example, one or more of (iii)-(vi).

In some embodiments of the invention, computer executable instructions further comprise a capability to indicate that the selected one or more products will be for household use.

In some embodiments of the invention, when an indication of household use is provided, the computer executable instructions further comprise a capability for obtaining an authorization to share prescription history and health information for one or more patients of the household and performing one or more of (iii)-(vi) for each patient where authorization is provided.

In some embodiments of the invention, when a serious or major interaction has been determined, the computer executable instructions further comprise a capability to advise the user one or more of that (a) the product is not recommended for purchase for the identified patient, (b) will prevent completion of the purchase of the selected interacting product, (c) the user may discuss the interaction alert with a pharmacist via telephone or other communication method (d) providing a user acknowledgement of the interaction and allowing the transaction to proceed, and/or (e) combinations thereof.

In some embodiments of the invention, computer executable instructions further comprise a capability to alert the user to one or more interactions selected from one or more of: drug-drug interaction, severe drug-drug interaction, drug-disease interaction wherein the disease is reported by the user, drug-inferred disease interaction, drug-allergy interaction, drug-food interaction, drug-environment interaction and/or drug-lifestyle interaction.

In some embodiments of the invention, when an interaction has been identified, the computer executable instructions further comprise a capability to suggest alternative safer OTC products. In some embodiments of the invention, interaction alerts are provided as messaging at the interaction pair level.

In some embodiments of the invention, a DUR user interface is capable of providing more detailed patient condition information. In some embodiments of the invention, access is available to the user through a mobile device operating on a system selected from the group consisting of PC, MAC, ANDROID and Blackberry.

In some embodiments of the invention, computer executable instructions further comprise a capability to store the DUR transaction information including alerts triggered when interactions are identified, messages, history comprising information selected from the group consisting of alerts triggered, messages, alternative product suggestions, drug pairs and dates of alerts. In some embodiments of the invention, a capability is provided to electronically transfer prescription history into the drug interaction checker.

In some embodiments of the invention, a capability is provided for the user to provide information pertaining to the patient for use in the interaction checker selected from the group consisting of: prescription history, self reported OTC products, diseases, food and alcohol consumption, vitamin consumption, environment, and lifestyle. In some embodiments of the invention, a capability is provided to monitor expiration dating of prescription and OTC products and send alerts when the product shelf-life has expired.

In some embodiments of the invention, a capability is provided to delete information pertaining to a patient. In some embodiments of the invention, a capability is provided for the user to electronically scan a image corresponding to an OTC product or a prescription label, and/or a capability to convert the scanned image into electronic data corresponding to the drug associated with the label. In some embodiments of the invention, a capability is provided for storage of the drug information in the patient's drug history and to perform real-time DUR.

In some embodiments of the invention, a computer implemented method of drug interaction checking, comprising at least one of the sequential, non-sequential or sequence independent steps of electronically receiving by a computer a selection from a computer user device used by a customer of at least one over the counter (OTC) product for purchase by the customer, and identifying by the computer the at least one OTC product selected for purchase by the customer during, products that could potentially interact with at least one of a patient condition, prescription and another OTC product of a patient.

In some embodiments of the invention, the computer implemented method, executed by a computer, receives electronic authorization to access information about a prescription history, medical profile and other health condition of the patient, and determines via responses to questions presented to the customer whether the patient will be using the at least one OTC product for one-time episodic use or on an ongoing basis.

In some embodiments of the invention, the computer implemented method, executed by a computer, compares a combination of the at least one OTC product and the information available from the patient's prescription and medical history against a list of possible drug interactions stored in one or more rules databases, identifies drug interactions responsive to said comparing, and alerts at least one of the customer and the patient of the drug interactions responsive to said identifying the drug interactions.

In some embodiments of the invention, the computer implemented method, executed by a computer, further comprises obtaining an authorization to share prescription history and health information for one or more patients of a household. In some embodiments of the invention, the computer implemented method, executed by a computer, determines a serious or major interaction, alerts the customer that the selected product is not recommended for purchase for the identified patient, prevents completion of the purchase of the selected interacting product and/or provides the customer acknowledgement of the interaction and allowing the transaction to proceed.

In some embodiments of the invention, the computer implemented method, executed by a computer, alerts the user to one or more interactions selected from at least one of: drug-drug interaction, severe drug-drug interaction, drug-disease interaction wherein the disease is reported by the user, drug-inferred disease interaction, drug-allergy interaction, drug-food interaction, drug-environment interaction and/or drug-lifestyle interaction.

In some embodiments of the invention, the computer implemented method, executed by a computer, transmits to the customer an alternative safer OTC product. In some embodiments of the invention, the computer implemented method, executed by a computer, receives from the customer information pertaining to the patient for use in the interaction checker including at least one of: prescription history, self reported OTC products, diseases, food and alcohol consumption, vitamin consumption, environment, and lifestyle. In some embodiments of the invention, the computer implemented method, executed by a computer, monitors expiration date of prescription and OTC products purchased and sending alerts when the product shelf-life has expired.

BRIEF DESCRIPTION OF THE DRAWINGS

Additional embodiments of the invention, its nature and various advantages, will be more apparent upon consideration of the following detailed description, taken in conjunction with the accompanying drawings, in which like reference characters refer to like parts throughout, and which include the following:

FIG. 1 is an illustration of pre-authenticated token delivery according to some embodiments of the invention.

FIG. 2 is an illustration of data flow overview according to some embodiments of the invention.

FIG. 3 is an illustration of the drug interaction checker process: identifying Drug Utilization Review items in the cart according to some embodiments of the invention.

FIG. 4 is an illustration of the drug interaction checker process: information sharing authorization according to some embodiments of the invention.

FIG. 5 is an illustration of the drug interaction checker process: determining product use according to some embodiments of the invention.

FIG. 6 is an illustration of the drug interaction checker process: determining product use according to some embodiments of the invention.

FIG. 8 is an illustration of the drug interaction checker process: results page messages (yellow notification example) according to some embodiments of the invention.

Figure 9:
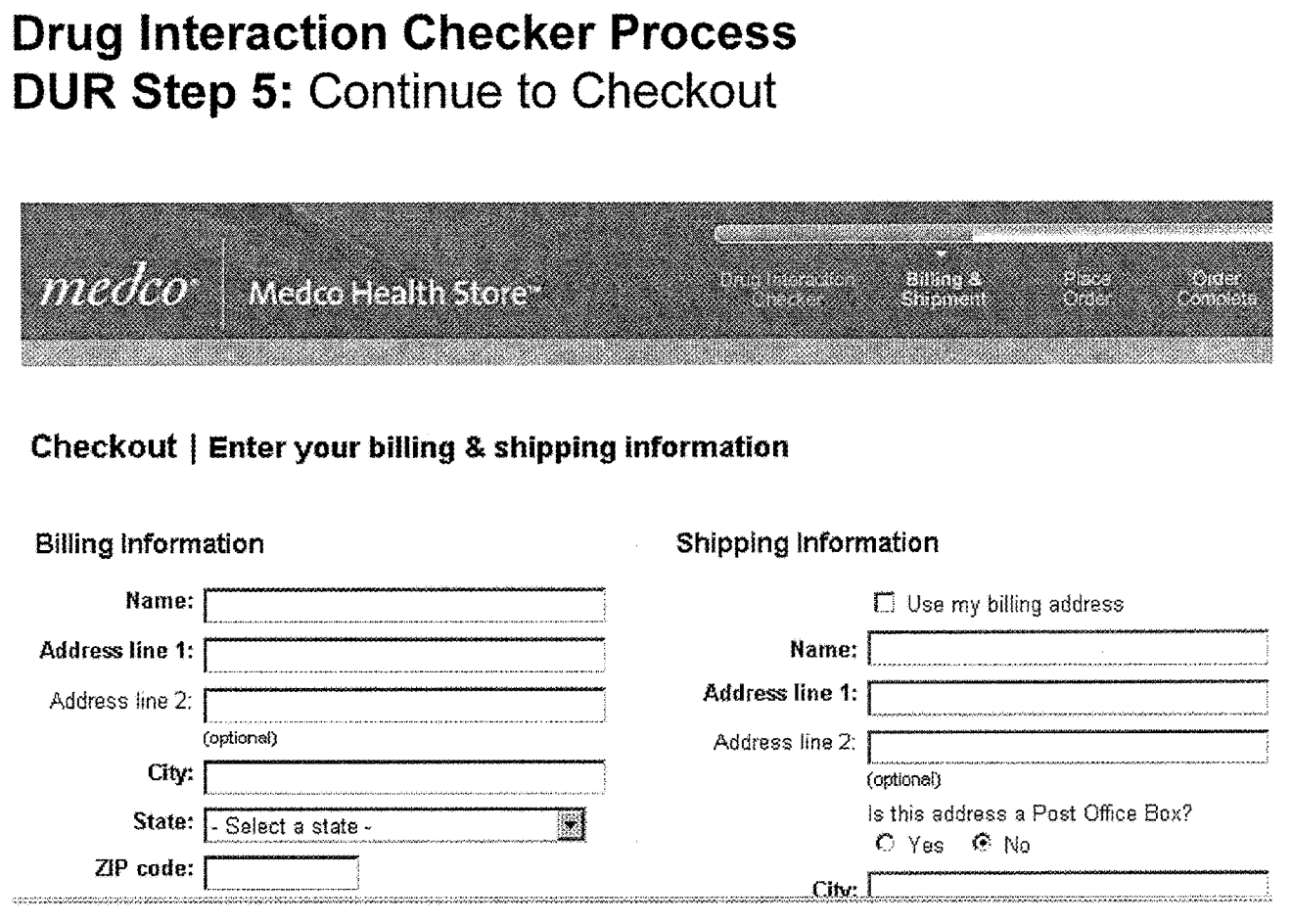

FIG. 9 is an illustration of the drug interaction checker process: checkout according to some embodiments of the invention.

Figure 10:
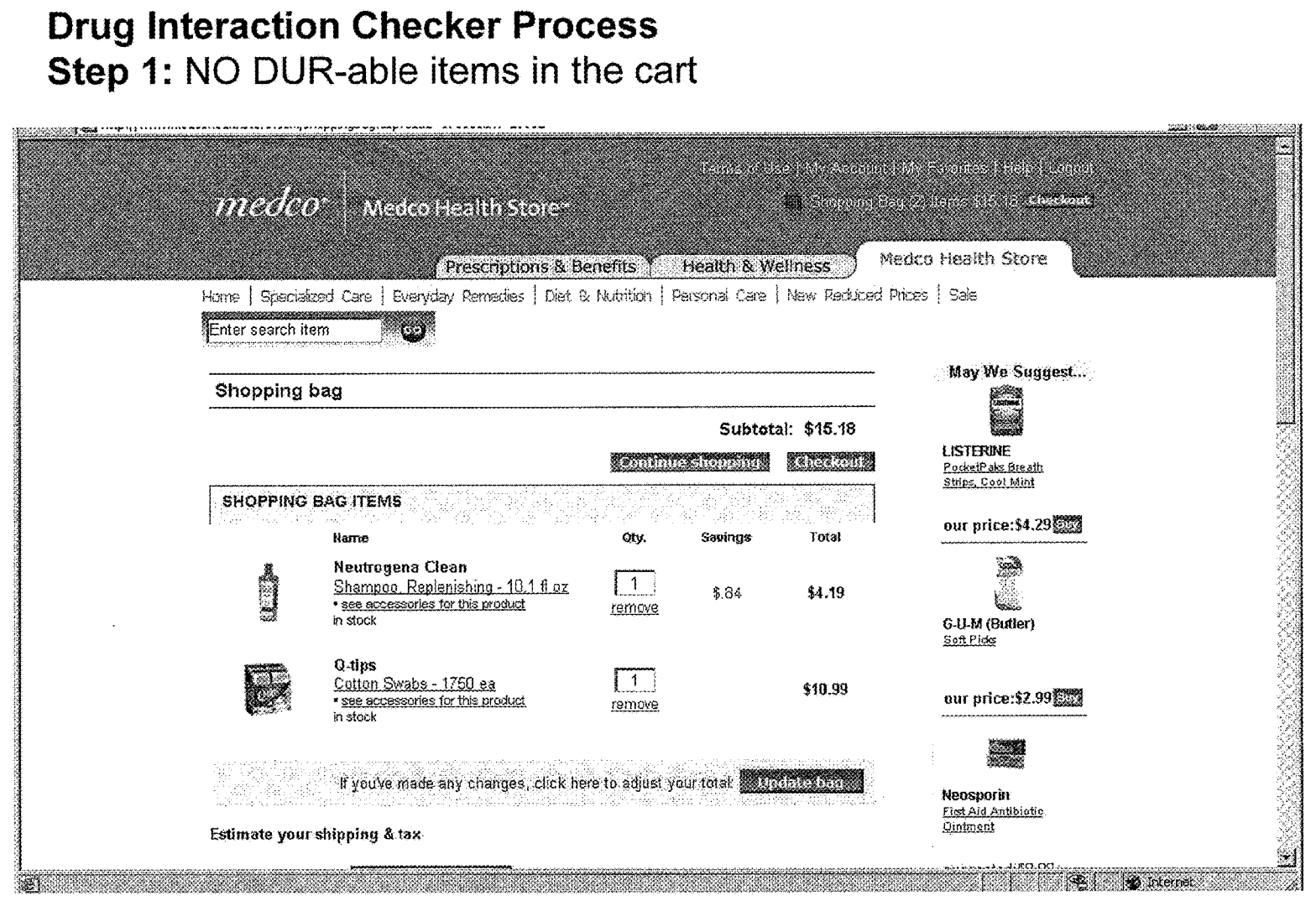

FIG. 10 is an illustration of the drug interaction checker process: no Drug Utilization Review items in the cart according to some embodiments of the invention.

Figure 11:
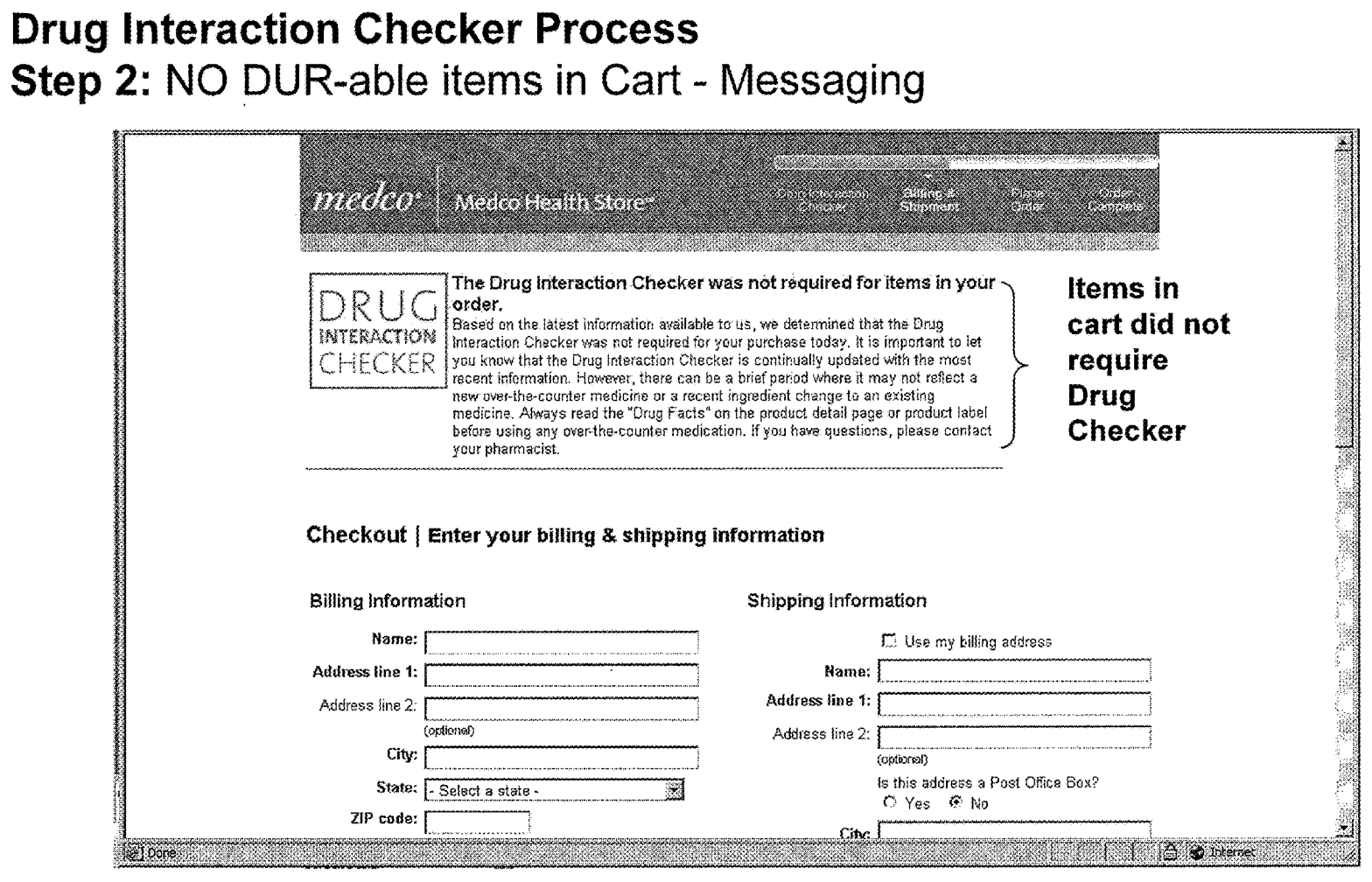

FIG. 11 is an illustration of the drug interaction checker process: No Drug Utilization Review items in the cart messaging according to some embodiments of the invention.

FIG. 16 is an illustration of the business rules according to some embodiments of the invention.

DETAILED DESCRIPTION OF PREFERRED EMBODIMENTS OF THE INVENTION

Figure 7:
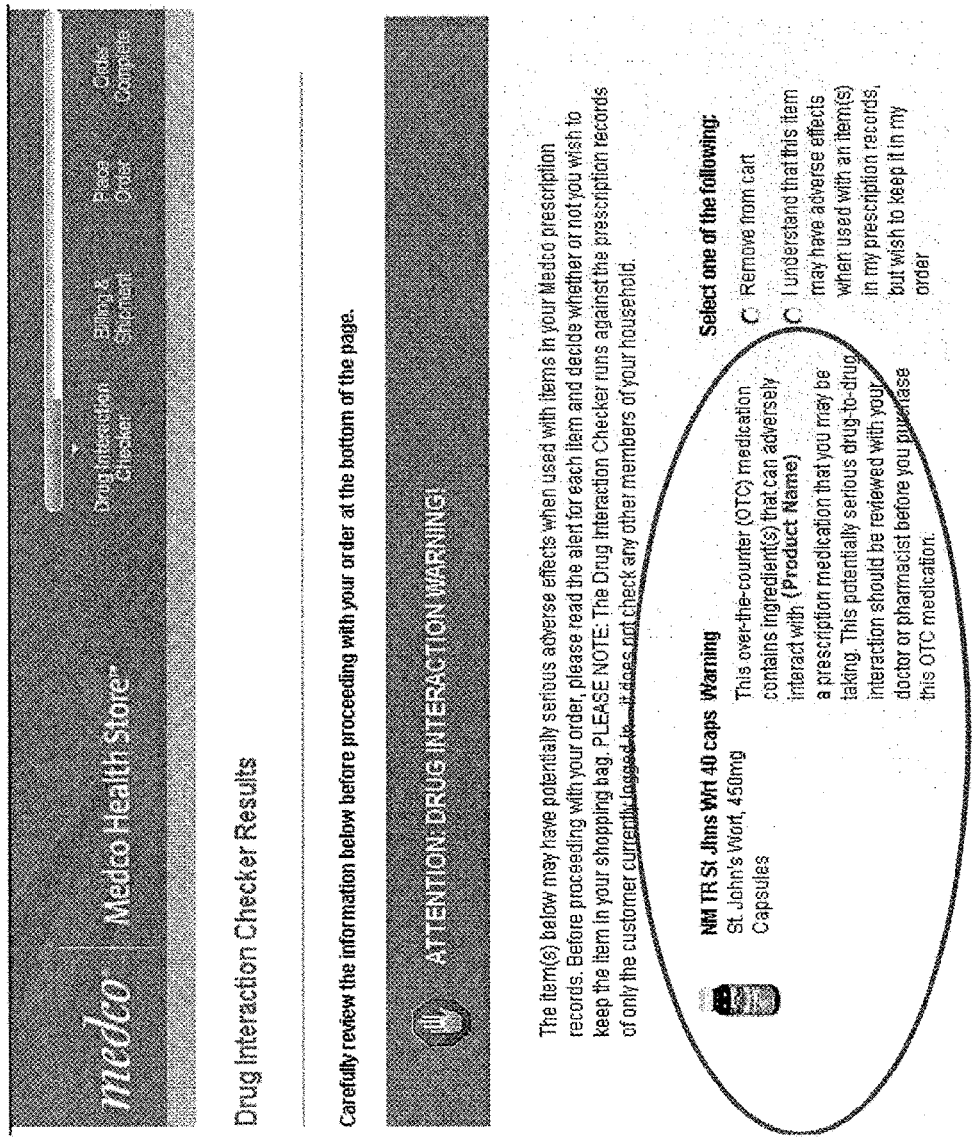
FIG. 7 is an illustration of the drug interaction checker process: results page messages (red warning example) according to some embodiments of the invention.

Before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the invention be regarded as including equivalent constructions to those described herein insofar as they do not depart from the spirit and scope of the present invention. For example, the specific sequence of the described process maybe altered so that certain processes are conducted in parallel or independent, with other processes, to the extent that the processes are not dependent upon each other. Thus, the specific order of steps described herein is not to be considered implying a specific sequence of steps to perform the process. In alternative embodiments, one or more process steps may be implemented by a user assisted process and/or manually. Other alterations or modifications of the above processes are also contemplated. For example, further insubstantial approximations of the process and/or algorithms are also considered within the scope of the processes described herein.

In addition, features illustrated or described as part of one embodiment can be used on other embodiments to yield a still further embodiment. Additionally, certain features may be interchanged with similar devices or features not mentioned yet which perform the same or similar functions. It is therefore intended that such modifications and variations are included within the totality of the present invention.

The present invention relates to a computer system and computer implemented method for real-time drug interaction screening for users buying OTC drugs through the internet where they would not have direct access to a pharmacist to discuss the potential interactions information specific to a patient.

Patient Information Used to Check Against a Drug Selection

In certain embodiments, patient information is available from a prescription history or profile maintained by the pharmacy where the patient orders prescription medications. In the case of certain pharmacy benefits managers ("PBM"), with a dispensing pharmacy service, the prescription records can be obtained from multiple sources. A PBM could also possess and access claim data for all dispenses from its own dispensing pharmacy service as well as all claim data for prescriptions filled by other pharmacies, e.g., community pharmacies that submit claims to the PBM for dispensing.

In certain embodiments, the PBM may also access medical claims data from the patient's health plan. Typically this data is accompanied by diagnosis codes which could be used to identify a patient's disease state. Additionally, lab values and other diagnostic information could be used to determine the suitability of certain drug therapies based on a patient's unique genetic and metabolic characteristics. Details of such processes are described in commonly assigned U.S. Pat. Nos. 7,711,583 and 7,124,031, the disclosures of which are hereby incorporated by reference in their entireties.

In certain embodiments the information is self reported by the patient. There may be instances where a patient chooses to obtain prescription medication via a pharmacy or a transaction that is not associated with the PBM pharmacy service or a reimbursement. In these cases, the invention includes capability for the user to search and select drugs currently being utilized. Additionally, where OTC products are purchased outside of the PBM network, those products could also be added to a patient's profile maintained by the PBM. In other examples, the patient has no affiliation with the PBM and loads his drug, disease and other pertinent information into a patient profile in order for the drug interaction checker to perform DUR on a potential purchase.

In other embodiments, patient information including drug, food and excipient allergies, supplements and vitamins, food, alcohol, environment and lifestyle are included in the patient profile for consideration during a DUR.

In other embodiments, the drug interaction checker allows for point of use, and one by one loading of drugs or other pertinent patient information for DUR screening.

In still other embodiments, information is obtained with a DUR interface capability allowing the system to clarify reported patient conditions. In some cases, patients report a drug allergy where the experience was actually a known side effect. One common example is a reported codeine allergy when the patient experienced stomach discomfort, not an allergic reaction. Listing a codeine allergy may prevent a patient from receiving a similar drug that has a much lower incidence of stomach irritation due to the nature of the active ingredient, route of administration or delivery formulation.

DUR Rules for Checking Against Patient Drug and Other Pertinent Information

A person having ordinary skill in the art such as a licensed pharmacist would readily appreciate the clinical information concerning interactions of drugs with all of the aforementioned patient specific information. In certain preferred embodiments of the invention, the drug interaction rules and alerts are obtained from commercially available databases such as First DataBank, San Francisco, Calif. In certain more preferred embodiments of the invention, the alerts are modified to be more readily understood by non-clinical users. In still other preferred embodiments, the rules and alerts comprise a combination of commercially available information, customization obtained from medical literature, official compendia, and manufacturer labeling. In certain preferred embodiments different rule collections are stored in different databases and can be accessed by the system individually or in combination in a given DUR checking process.

In certain other embodiments of the invention, the DUR rules are capable of distinguishing between a one-time fill of a prescription drug and a cumulative use. In certain cases, the risk of interaction increases with cumulative use because the plasma concentrations can rise over continuous use. In other examples, enzymes involved in drug activation or elimination can be increased or decreased by certain drug therapies with cumulative use.

In certain preferred embodiments, the information needed to perform the drug interaction checker is continuously available and upgraded. An example of such object data grid is described in commonly assigned U.S. patent application Ser. No. 13/296,825 filed on Nov. 15, 2011, the disclosure of which is hereby incorporated by reference in its entirety.

Identifying Potentially Interacting Products

While it will be readily understood by a person of ordinary skill, certain OTC products can potentially lead to drug interactions. However, in certain embodiments of the invention, certain products available through the web-based commerce platform have no potential for drug interaction. Typical products would include those devoid any pharmacological agent such as surgical tape or cotton swabs. In these cases, the system and process of the invention comprises capability to exclude these products from a DUR check while identifying products that are intended to come in contact with the body, typically via oral ingestion, and contain a pharmacologically active agent.

Authorization to Share Patient Drug History and Other Information

In certain embodiments of the invention the system and process is capable of obtaining an authorization to share prescription drug information, as well as all other pertinent patient information described herein. In certain preferred embodiments, the authorization complies with any and all state and federal privacy requirements prior to the information being submitted to the drug interaction checker.

Acute or Chronic Designation.

The designation by the user of a selected OTC product as acute or chronic would be readily understood by a person having ordinary skill in the art to have a readily understood timeframe based on the drug and condition for being treated. Acute use is one time or single episodic use for a condition that subsides in a short time, typically about 1-14 days, more preferably about 1-5 days. For the purposes of the present invention, chronic use is meant to include use for a duration. longer than acute use. In certain embodiments, about 5 days to about 2 years, or more preferably about 2 weeks to about 12 months.

In certain preferred embodiments, a chronic designation would be added to the patient's drug profile for consideration in subsequent DUR screens. In other preferred embodiments, OTC products intended for acute use are not saved in the patient's drug history.

Drug Interaction Screening/Identification/Alerting

Drug interaction screening would allow the one' or more products to be compared against all relevant drug data. Where the rules identify an interaction and associated severity level, an alert is communicated to the user.

In certain preferred embodiments where an identified interaction is severe, the invention comprises the capability to advise the user (a) the product is not recommended for purchase for the identified patient, (b) will prevent completion of the purchase of the selected interacting product, (c) the user may discuss the interaction alert with a pharmacist via telephone or other communication method (d) providing a user acknowledgement of the interaction and allowing the transaction to proceed, or (e) combinations thereof.

Suggestion of Alternative Safer Options

In certain preferred embodiments of the invention, the system and process has the capability to suggest a safer product than the OTC product selected by the user. One of ordinary skill in the art will readily appreciate such alternatives, and would generally include those that don't interact with the given element or elements specific to the patient's information leading to the interaction. By way of example, a patient may be allergic to aspirin. Where the patient information is devoid of elements leading to an interaction with acetaminophen, the system would suggest a switch from aspirin to acetaminophen. Other permutations of interactions and safer suggestions would be readily known to those having ordinary skill the pharmaceutical arts or access to such information in regular pharmacy practice settings.

Drug Safety Check shall be performed during the checkout process on the Store site:

Drugstore to submit a request to the Medco/Rules Service

Medco/Rules Service to execute the Drug Safety Check

Medco to send results back to Drugstore

Drugstore to display (if any) alerts/warning messages to the user

Three high level services will be invoked by the DrugStore System when a user checks out some products on the Store's site.

1) UPC/NDC Mapper Service
2) Drug Safety Check Service
3) Logging Service

An additional service is exposed to renew the LTPA Session Token when the user navigates across DrugStore's site—since the initial token is only valid for 30 minutes, this 'Heartbeat' service can keep the session alive so that the user can successfully navigate back to Medco's site as needed.

KeepSession Service

Initial LTPA Token Delivery

The request for data is initiated by a user using an internet application and requesting for data, which is then received by the DrugStore's server. The DrugStore server receives the request and then decides if it needs information from Medco, and then initiates an XML Request to a predefined Medco Web Service Endpoint. The authentication and authorization is done by means of an LTPA (Lightweight Third-Party Authentication) token that is issued by the Medco's System and which is included in the SAML Packet during the initial SSO Cross-over from Medco.com to DrugStore.com.

In the first step as illustrated in FIG. 1, during the transfer from Medco's site to the DrugStore site via SSO, the LTPA token is included in the SAML packet along the other existing data. The DrugStore application is then responsible for passing the LTPA Token in all requests from then on.

As illustrated in FIG. 2, after receiving the token, DrugStore can call Medco's services for additional information to fulfill the user's activity on the DrugStore.com site as required. The LTPA Token is required for each request (Set in a specific HTTP Header given in the implementation section)

Each successful request then renews the token and a new token is sent back, DrugStore must ensure that the new token is then used in all subsequent requests to prevent session timeout.

A mapper service maps given UPCs to their corresponding NDCs. This does not return the alert messages, but rather just returns all the NDCs for the products that are "DURable". This service will be invoked only for the first time when the Drug Safety Check Indicator is null in the user's profile at DrugStore. The user will be prompted by the DrugStore's website for this information and all consequent calls would be based on it. The user will also be provided with an option of updating the Indicator on DrugStore's website.

Figure 12:
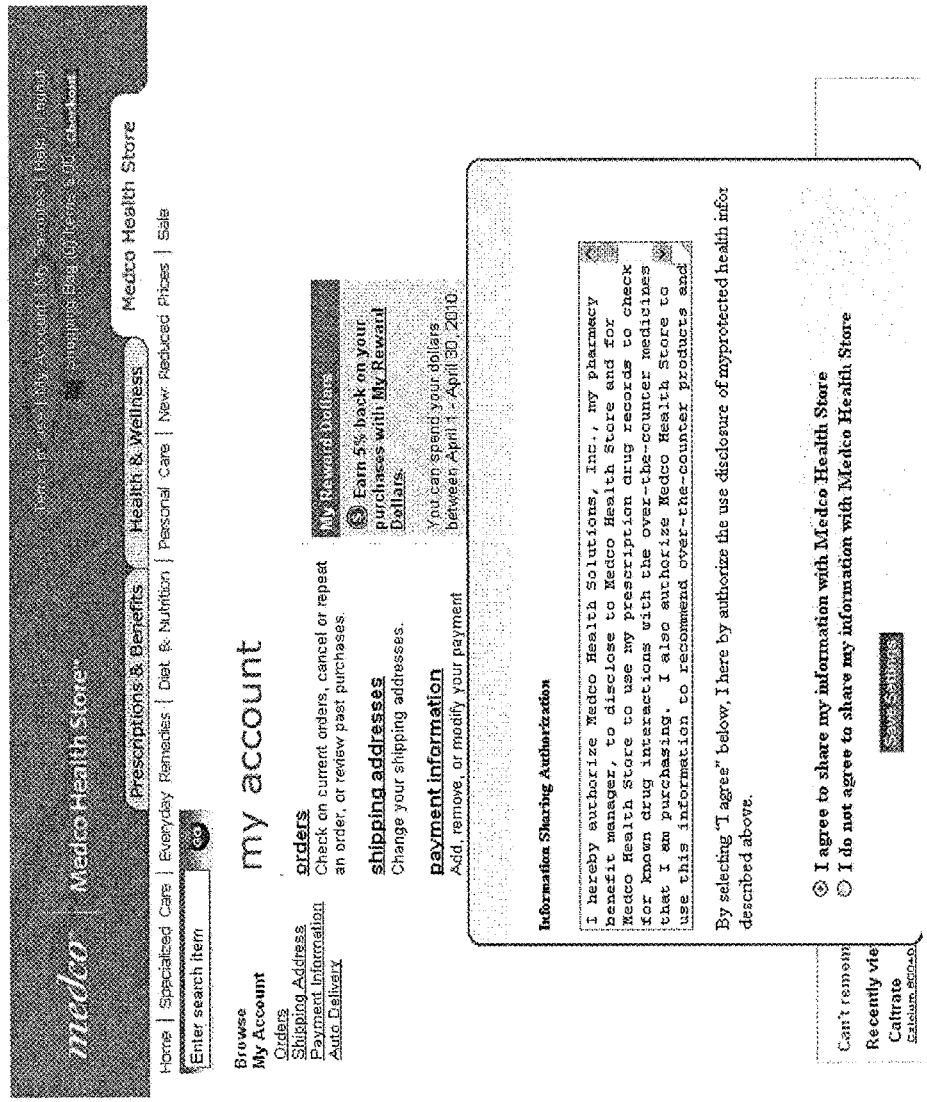
FIG. 12 is an illustration of the drug interaction checker: updating information sharing preference according to some embodiments of the invention.
Figure 13:
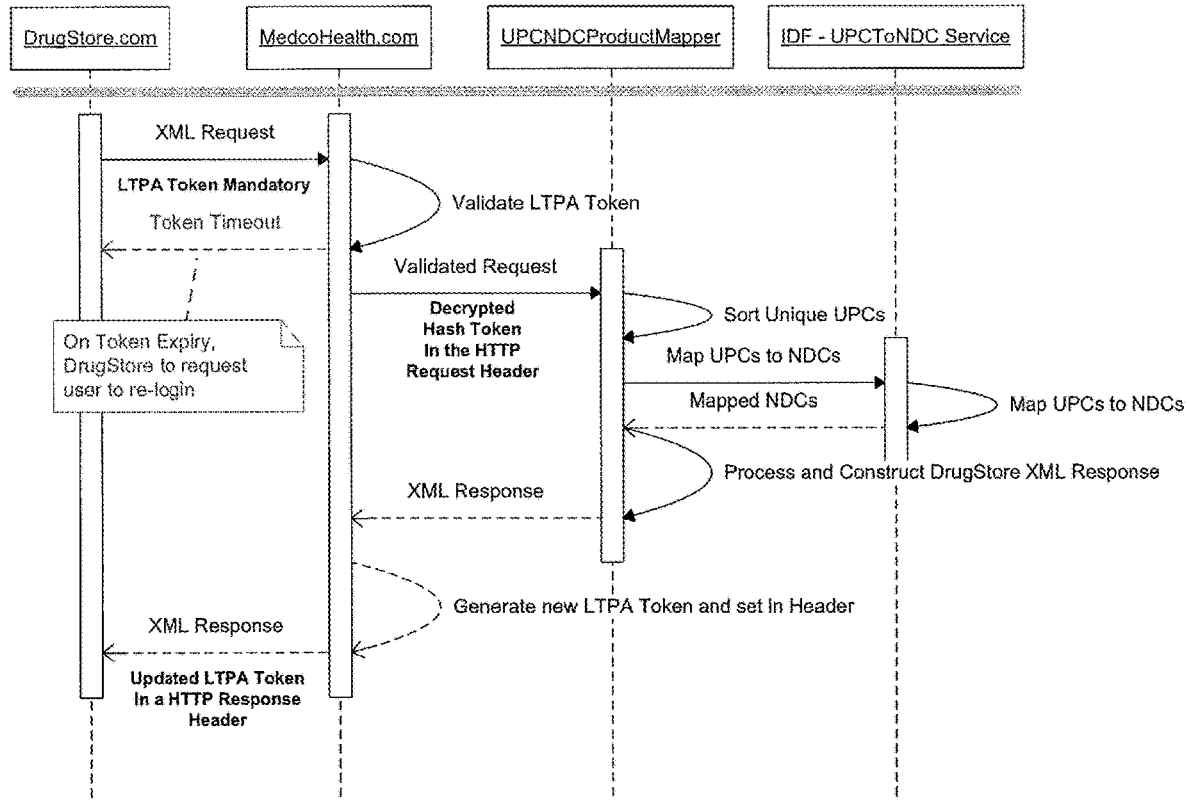
FIG. 13 is an illustration of the Product Mapper Service according to some embodiments of the invention.
Figure 14:
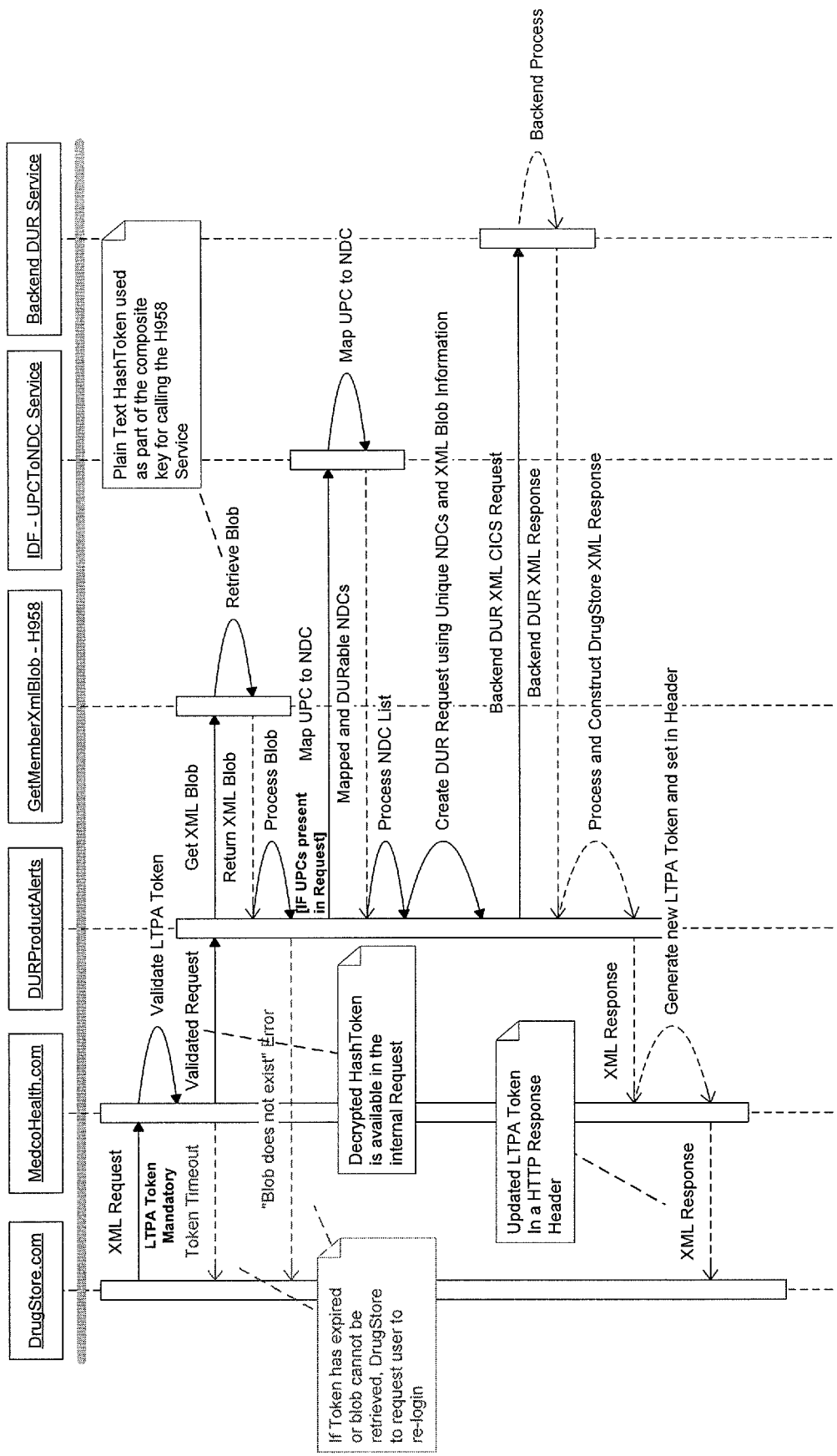
FIG. 14 is an illustration of the Drug Utilization Review Product Alerts Service according to some embodiments of the invention.
Figure 15:
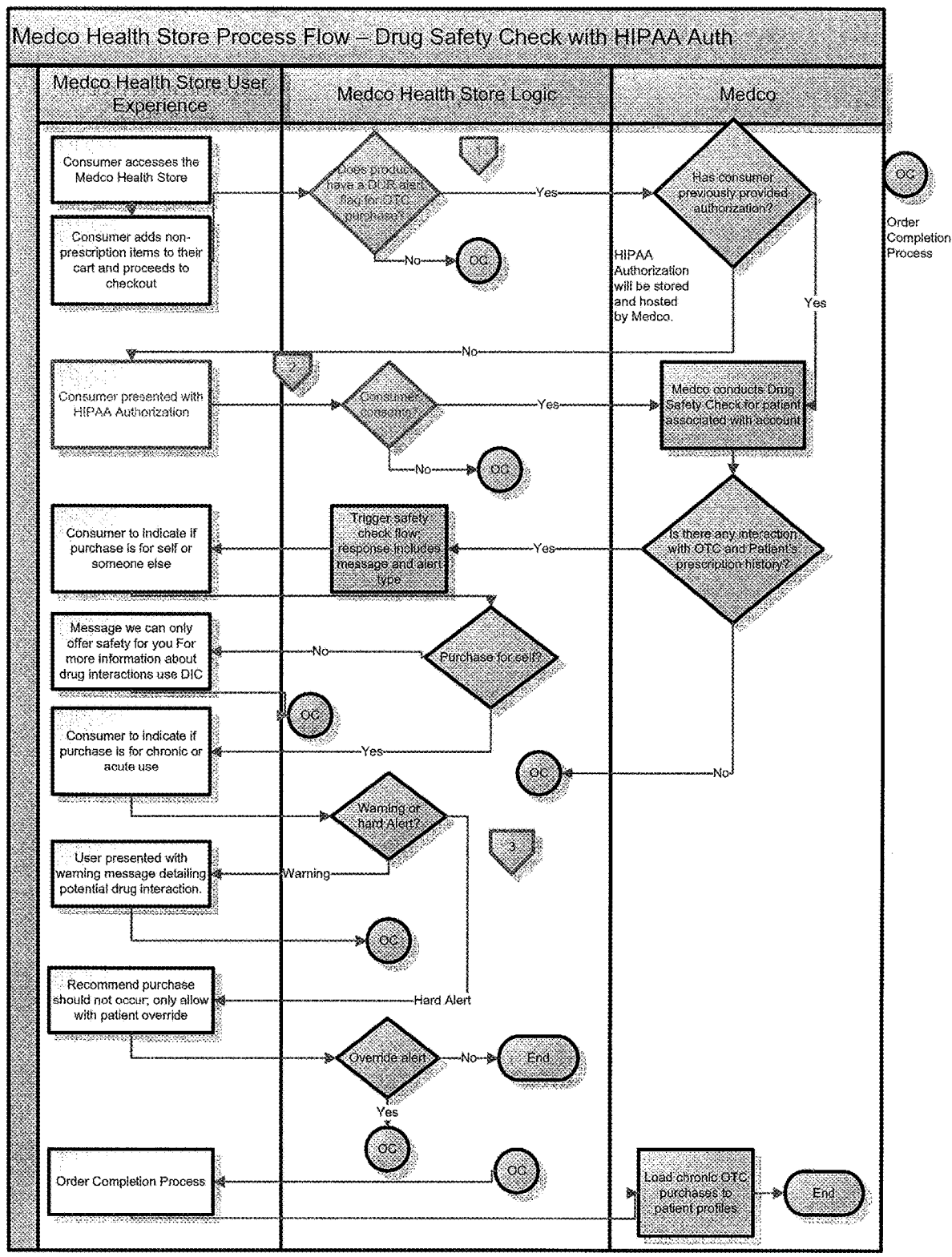
FIG. 15 is an illustration of the drug safety check with Health Insurance Portability and Accountability Act Authorization according to some embodiments of the invention.

If there are changes to the items in the shopping cart of the user and if DrugStore has already had the UPCs mapped to their NDCs, then DrugStore should send Medco the corresponding NDCs that were previously returned to avoid unnecessary duplicate calls that may need to be done by Medco's systems in order to map the UPCs to their corresponding NDCs again. The logical process flows are illustrated in FIGS. 12-13.

Request:

The request is an XML Body POST sending the UPC numbers.

| Field Name | Length | Description |
| --- | --- | --- |
| Request | | Root node |
| TestMode | 1 | Test Mode functionality, If "Y", returns a canned XML Response |
| Format | 4 | Always "xml" - Indicates the format of the response, Default is "json", should be always present in this setup. |
| Channel | 3 | Used for defaulting values needed by Medco's internal systems based on the caller, Should be "CI-IP" in this case |
| UPC occurs n times | 12 | The standard 12-digit UPC number with prefix and check-digit. The 10-digit UPC (without Prefix and check-digit) for which a corresponding NDC must be mapped by Medcci, Occurs 0 to n times (Upper Limit 50) |

Sample XML Request:

```
<?xml version="1.0" encoding="UTF-8"?>
<Request>
    <Format>xmk/Format>
    <Channel>CHP</Channel>
    <UPC>123456789011</UPC>
    <UPC>123456789012</UPC>
    <UPC>123456789013</UPC>
</Request>
```

Response:

The Response is an XML Response that is returned, along with an updated LTPA Token which can be stored internally by DrugStore.

The updated token is in a "Set-Cookie" HTTP Response Header having the corresponding value for the key "Ltpa-Token2", the value alone can be extracted and used for all consequent requests to Medco's System.

Ex: Set-Cookie: LtpaToken2=<new_token_value>; other=params

| Field Name | Length | Description |
| --- | --- | --- |
| Response | | Root node |
| StatusCode | 4 | Status Code of the Current Transaction "0000" - Success "0002" - No DURable NDCs found for all the UPCs "9999" - Corresponds to System Error message "1900" - Session Timeout/LTPA Token error (DrugStore should prompt user to re-login) |
| StatusMessage | | Status Message of the Current Transaction "Success" - If StatusCode is "0000" "No DURable NDCs were found" - If StatusCode is "0002" Status Message will be dynamic and corresponds to the failure - StatusCode "9999" This Node is not available if there is a Token Timeout |
| Token | | Present on Token timeout, Can be ignored - currently blank, comes from the Main Proxy service |
| RoutingUrl | | Present on Token timeout, Can be ignored - currently blank, comes from the Main Proxy service |
| RoutingParams | | Present on Token timeout, Can be ignored - currently blank, comes from the Main Proxy service |
| ErrorMessage | | Present on Token timeout, Can be ignored - currently blank, comes from the Main Proxy service, |
| Product occurs n times | | Wrapper Node for UPC to NBC Maps (Under Response) |
| UPC | 12 | The UPC that was in the original Request as a key (Under Product) |
| NDC | 11 | The NDC for the corresponding UPCs (Under Product) Blank if no corresponding NDC is found for a given UPC Ex: <NDC/> |

Sample XML Response:

```
<?xml version="1.0" encoding="UTF-8"?>
<Response>
    <StatusCode>0000</StatusCode>
    <StatusMessage>Success</StatusMessage>
    <Product>
        <UPC>123456789011</UPC>
        <NDC>01234567890</NDC>
    <Product>
    <Product>
        <UPC>123456789012</UPC>
        <NDC>01234567891</NDC>
    </Product>
    <Product>
        <UPC>123456789013</UPC>
        <NDC/>
    </Product>
</Response>
```

The Drug Safety Check Service is a service that will return all the alert messages for a given product based on its interactions with other drugs that are already prescribed or are present in the member's profile. These alert messages facilitate DrugStore to display alert messages to the user so that they may chose to continue or abort their purchase depending on the severity of the messages.

Request:

The request is an XML Body POST sending the NDC numbers and UPC numbers that are to be checked for the interactions with other drugs. If DrugStore had previously mapped come UPCs to their NDCs in the current session, they should ideally send Medco the NDCs to avoid a duplicate lookup again.

| Field Name | Length | Description |
|---|---|---|
| Request | | Root node |
| TestMode | 1 | Test Mode functionality, If "Y", returns a canned XML Response |
| Format | 4 | Always "xml" - Indicates the format of the response, Default is "json", should be always present in this setup. |
| Channel | 3 | Used for defaulting values needed by Medco's internal systems based on the caller, Should be "CHP" in this case |
| UPC occurs n times | 12 | The standard 12-digit UPC number with prefix and check-digit. The 10-digit UPC (without Prefix and check-digit) for which a corresponding NDC must be mapped by Medco, Occurs 0 to n times (Upper Limit 50) |
| NDC occurs n times | 11 | The NDC if available already, this will be used to perform the Drug Safety Check. Occurs 0 to n times (Upper Limit 50) |

Sample XML Request:

```
<?xml version="1.0" encoding="UTF-8"?>
<Request>
    <Format>xml</Format>
    <Channel>CHP</Channel>
    <UPC>123456789015</UPC>
    <NDC>52421145645</NDC>
</Request>
```

Response:

The Response is an XML Response that is returned, along with an updated LTPA Token which can be stored internally by DrugStore.

The updated token is in a "Set-Cookie" HTTP Response Header having the corresponding value for the key "Ltpa-Token2", the value alone can be extracted and used for all consequent requests to Medco's System.
Ex: Set-Cookie: LtpaToken2=<new_token_value>; other=params

| Field Name | Length | Description |
|---|---|---|
| Response | | Root node |
| StatusCode | 4 | Status Code of the Current Transaction |
| | | "0000" - Success |
| | | "0002" - No DURable NDCs were found |
| | | "1900" - Session Timeout/LTPA Token error (DrugStore should prompt user, to re-login) |
| | | "3000" - Blob cannot be retrieved (Very rare error - If this occurs, re-logging in should fix it, take same action as 1900) |
| | | "9999" - Corresponds to System Error message |
| StatusMessage | 50 | Status Message of the Current Transaction "Success" - If StatusCode is "0000" "No DURable NDCs were found" - If StatusCode is "0002" "Blob cannot be retrieved" - If StatusCode is "3000" Status Message will be dynamic and corresponds to the failure - StatusCode "9999" This Node is not available if there is a Token Timeout |
| Token | | Present on Token timeout, Can be ignored - currently blank, comes from the Main Proxy service |
| RoutingUrl | | Present on Token timeout, Can be ignored - currently blank, comes from the Main Proxy service |
| RoutingParams | | Present on Token timeout, Can be ignored - currently blank, comes from the Main Proxy service |
| ErrorMessage | | Present on Token timeout, Can be ignored - currently blank, comes from the Main Proxy service |
| Product (occurs n) | | One node for each matching DURable NDC, under Response |
| UPC | 12 | UPC for the matching Product (under Product) If available in the request |
| NDC | 11 | NDC for the matching Product (under Product) |
| Name | 25 | The Name of the Drug (under Product) |
| Alert (Occurs n) | | Wrapper node for Alert Information, (under Product) |
| ConflictCde | 2 | Conflict Code of the Interacting Product (under Alert) |
| CategoryCde | 3 | Category Code of the Interacting Product (under Alert) |
| SeverityCde | 1 | Severity Code of the Interacting Product (under Alert) |
| InteractingDrug | 25 | The Drug whose constituents consist of this NDC (under Alert) |
| WarningLevelInd | 1 | The Red/Yellow Indicator that this message should display in (under Alert) 0 for None 1 for Yellow 2 for Red |
| Message | | Wrapper Node for the actual alert Message, (under Alert) |
| Text | 750 | The actual text of the error message, (under Message) |

Sample Response XML:

```
<?xml version="1.0" encoding="UTF-8"?>
<Response>
    <StatusCode>0000</StatusCode>
    <StatusMessage>Success</StatusMessage>
    <Product>
    <UPC>123456789015</UPC>
    <NDC>72432910778</NDC>
    <Name><[CDATA[POTASSIUM CHLORIDE]]></Name>
    <Alert>
        <ConflictCde>DD</ConflictCde>
        <CategoryCde>DD3 </CategoryCde>
        <SeverityCde>3</SeverityCde>
```

```
            <InteractingDrug><![CDATA[ENALAPRIL]]></InteractingDrug>
            <WarningLevelInd>l<WarningLevelInd>
            <Message>
                <Text></[CDATA[This over the counter (OTC)
medication may adversely interact with a prescription medication ENALAPRIL that you are also
taking. These potential interactions should be reviewed by your doctor before making changes in
therapy.]]></Text>
            </Message>
        </Alert>
        <Alert>
            <ConflictCde>DD<ConflictCde>
            <CategoryCde>DD3</CategoryCde>
            <SeverityCde>3</SeverityCde>
            <InteractingDrug><![CDATA[DIOVAN]]></InteractingDrug>
            <WarningLevelInd>1</WarningLevelInd>
            <Message>
                <Text></[CDATA[This over the counter (OTC)
medication may adversely interact with a prescription medication DIOVAN that you are also
taking. These potential interactions should be reviewed by your doctor before making changes in
therapy.]}><Text>
            </Message>
        </Alert>
    </Product>
    <Product>
        <NDC>52421145645</NDC>
        <Name><[CDATA[EPIPEN JR]]><Name>
        <Alert>
            <ConflictCde>DD<ConflictCde>
            <CategoryCde>SDD</CategoryCde>
            <SeverityCde>l<SeverityCde>
    <InteractingDrug><![CDATA[NORMODYNE]]></InteractingDrug>
            <WarningLevelInd>2</WarningLevelInd>
            <Message>
                <Text><![CDATA[This over the counter (OTC)
medication may adversely interact with a prescription medication NORMODYNE that you are
also taking. These potential interactions should be reviewed by your doctor before making
changes in therapy.]]></Text>
            <Message>
        </Alert>
    </Product>
</Response>
```

A Logging Service is optionally provided that can be used to update a member's profile based on what the member has checked out if it has any interactions with other Drugs. This is primarily for Self Reported OTC logging and CCF (used for Customer Service Tracking) on Medco's end and updates the Member's profile.

This Service will be invoked every time irrespective of whether the Drug Safety Check was called when the Order is confirmed or checked out at the DrugStore Online Store.

Request:

The request is an XML Body POST having the necessary fields as documented below.

| Field Name | Length | Description |
| --- | --- | --- |
| Request | | Root node |
| TestMode | 1 | Test Mode functionality, If "Y", returns a canned XML Response |
| Format | 4 | Always "xml" - Indicates the format of the response, Default is "json", should be always present in this setup. |
| Channel | 3 | Used for defaulting to values needed by Medco's internal systems based on the caller, Should be "CHP" in this case |
| Order - Occurs 1 | | Parent node under Request |
| ConfirmationNbr | | Confirmation number |
| SessionId | 30 | BV SessionId |
| DURInd | 2 | DUR Indicator about the order (With DUR or Without DUR) 0 - Without DUR 1 - With DUR 99 - DUR call Failed |
| Product - Occurs n | | Product Wrapper node under Order |
| SelfInd | 1 | Product for Self Indicator |
| RegularBasisInd | 1 | Product taken on Regular Basis Indicator |
| UPC | 12 | UPC for the matching Product (under Product) The standard 12-digit UPC number with prefix and check-digit. |
| NDC | 11 | NDC for the matching Product (under Product) |
| Alert (Occurs n) | | Wrapper node for Alert Information, (under Product) |
| ConflictCde | 2 | Conflict Code of the Interacting Product (under Alert) |
| CategoryCde | 3 | Category Code of the Interacting Product (under Alert) |
| SeverityCde | 1 | Severity Code of the Interacting Product (under Alert) |
| InteractingDrug | 25 | The Drug whose constituents consist of this NBC (under Alert) |
| WarningLevelInd | 1 | The Red/Yellow Indicator that this message should display in (under Alert) 0 for None 1 for Yellow 2 for Red |

Sample XML Request:

```
<?xml version="1.0" encoding="UTF-8"?>
    <Request>
        <Format>xml</Format>
        <Channel>CHP</Channel>
        <Order>
<ConfirmationNbr>123455655544</ConfirmationNbr>
<SessionId>@@@@2028102284.1220626361@@@@</SessionId>
            <DURInd>1</DURInd>
    <Product>
        <SelfInd>1</SelfInd>
        <RegularBasisInd>1</RegularBasisInd>
        <UPC>123456789011</UPC>
        <NDC>01234567890</NDC>
        <Alert>
            <ConflictCde>DD</ConflictCde>
            <CategoryCde>DD3</CategoryCde>
            <SeverityCde>3</SeverityCde>
            <InteractingDrug>
                <![CDATA[ENALAPRIL]]>
                <InteractingDrug>
            <WarningLevelInd>1</WarningLevelInd>
        </Alert>
        <Alert>
            <ConflictCde>DD</ConflictCde>
            <CategoryCde>DD3</CategoryCde>
            <SeverityCde>3</SeverityCde>
            <InteractingDrug>
                <![CDATA[DIOVAN]]>
            </InteractingDrug>
            <WarningLevelInd>1</WarningLevelInd>
        </Alert>
    </Product>
    <Product>
        <SelfInd>1</SelfInd>
        <RegularBasisInd>1</RegularBasisInd>
        <UPC>123456789012</UPC>
        <NDC>01234567891</NDC>
        <Alert>
            <ConflictCde>DD</ConflictCde>
            <CategoryCde>DD1</CategoryCde>
            <SeverityCde>2</SeverityCde>
            <InteractingDrug>
                <![CDATA[NORMODYNE]]>
                <InteractingDrug>
            <WarningLevelInd>2</WarningLevelInd>
        </Alert>
    </Product>
    </Order>
</Request>
```

Response:

The Response is an XML Response that is returned, along with an updated LTPA Token which can be stored internally by DrugStore.

The updated token is in a "Set-Cookie" HTTP Response Header having the corresponding value for the key "LtpaToken2", the value alone can be extracted and used for all consequent requests to Medco's System.

Ex. Set-Cookie: LtpaToken2=<new_token_value>; other=params

| Field Name | Length | Description |
| --- | --- | --- |
| Response | | Root node |
| StatusCode | 4 | Status Code of the Current Transaction |
| | | "0000" - Success |
| | | "0001" - CCF Successful but Profile Update Failed |
| | | "0002" - Profile Update Successful but CCF Failed |
| | | "0003" - Both CCF and Profile Update Failed |
| | | "1900" - Session Timeout/LTPA Token error |
| | | "9999" - Corresponds to System Error message |
| | | "3000" - Blob cannot be retrieved (Very rare error) |
| StatusMessage | 50 | Status Message of the Current Transaction |
| | | "Success" - If StatusCode is "0000" |
| | | "CCF Successful but Profile Update Failed" - If StatusCode is "0001" |
| | | "Profile Update Successful but CCF Failed" - If StatusCode is "0002" |
| | | "Both CCF and Profile Update Failed" - If StatusCode is "0003" |
| | | "Blob cannot be retrieved" - If StatusCode is "3000" |
| | | Status Message will be dynamic and corresponds to the failure - StatusCode "9999" |
| | | This Node is not available if there is a Token Timeout |

Sample Response XML:

```
<?xml version="1.0" encoding="UTF-8"?>
<Response>
    <StatusCode>0000</StatusCode>
    <StatusMessage>Success</StatusMessage>
</Response>
```

A KeepSession Service is a service that allows an LTPA Session token to be renewed without any other backend action done by Medco. The sole purpose of this service is to renew a valid LTPA token and return a new token that is valid for an additional 30 minutes from the time it is generated. If the incoming token is invalid, a timeout xml message is returned.

Request:

The request is an XML Body POST having any well-formed XML, But since the Request/Format node should be "xml" to get an XML Response, it should be used here (instead of just any xml), without which the Medco Service would default to JSON.

| Field Name | Length | Description |
| --- | --- | --- |
| Request | | Root node |
| Format | 3 | Hardcoded as "xml" - Under Request |

Sample XML Request:

```
<?xml version="1.0" encoding="UTF-8"?>
<Request>
    <Format>xml</Format>
</Request>
```

Response:

The Response is an XML Response that is returned, along with an updated LTPA Token which can be stored internally by DrugStore to be reused in subsequent Medco Requests.

The updated token is in a "Set-Cookie" HTTP Response Header having the corresponding value for the key "LtpaToken2", the value alone can be extracted and used for all consequent requests to Medco's System.
Ex: Set-Cookie: LtpaToken2=<new_token_value>; other=params
Response

| Field Name | Length | Description |
|---|---|---|
| Response | | Root node |
| StatusCode | 4 | Status Code of the Current Transaction "0000" - Successfully renewed token, No StatusMessage is provided to keep the size of the response small. "1900" - Session Timeout/LTPA Token error |
| Token | | Present on Token timeout, Can be ignored - currently blank, comes from the Main Proxy service |
| RoutingUrl. | | Present on Token timeout, Can be ignored - currently blank, comes from the Main Proxy service |
| RoutingParams | | Present on Token timeout, Can be ignored - currently blank, comes from the Main Proxy service |
| ErrorMessage | | Present on Token timeout, Can be ignored - currently blank, comes from the Main Proxy service |

Sample Response XML:
The updated LTPA token is present in a Set-Cookie HTTP Response Header
Successful Response

```
<?xml version="1.0" encoding="UTF-8"?>
<Response>
    <StatusCode>0000</StatusCode>
</Response>
```

If Timeout (Ask User to Login)

```
<Response>
    <StatusCode>1900</StatusCode>
    <Token/>
    <RoutingUrl/>
    <RoutingParams/>
    <ErrorMessage/>
</Response>
```

Drugstore to ping the KeepSession service call before the valid LTPA Token expires i.e. 30 minutes. This will ensure the LTPA Token is always valid, never expires, and prevents the service call timeouts. Use the renewed/updated LTPA Token every time to pass in the service calls.

While the foregoing description and drawings represent the preferred embodiments of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

The invention claimed is:

1. A method comprising:
    receiving, via a network on a first computing device, purchase selection data reflecting an over-the-counter (OTC) drug product;
    transmitting, on the first computing device, a processing request to a second computing device in response to the determination that the purchase selection data requires additional information from the second computing device;
    receiving, on the first computing device, session authentication packet data in response to transmission of the processing request, the session authentication packet data including a token valid for a predetermined period of time;
    receiving, via the network on the first computing device, associated usage data reflecting a purchaser indication of whether the OTC drug product is for chronic use or acute use;
    in response to receipt of the associated usage data reflecting the purchaser indication that the OTC drug product is for chronic use, transmitting, on the first computing device, a drug utilization review (DUR) request and the token to the second computing device, the DUR request being a request to perform DUR based on the OTC drug product and patient claims data; and
    receiving, on the first computing device, a drug interaction alert based on performance of the DUR responsive to the token being valid.

2. The method of claim 1, further comprising:
    receiving, via the network on the first computing device, an additional token based on performance of the DUR responsive to the token being valid; and
    transmitting, on the first computer device, a logging request and the additional token to the second computing device.

3. The method of claim 1, wherein receipt of the purchase selection data and receipt of the associated usage data is from a user device.

4. The method of claim 1, wherein the session authentication packet data is a Security Assertion Markup Language (SAML) packet.

5. The method of claim 1, further comprising:
    fulfilling a purchase associated with the OTC drug product based on the purchase selection data; and
    storing purchase information associated with fulfillment of the purchase.

6. The method of claim 1, wherein the DUR request is a request to perform DUR based on a past OTC drug product, the OTC drug product, and the patient claims data.

7. The method of claim 1, wherein receipt of the purchase selection data is through a graphical user interface.

8. A method comprising:
    receiving, via a network on a first computing device, purchase selection data reflecting an over-the-counter (OTC) drug product;
    transmitting, on the first computing device, a processing request to a second computing device in response to the determination that the purchase selection data requires additional information from the second computing device;

receiving, on the first computing device, session authentication packet data in response to transmission of the processing request, the session authentication packet data including a token valid for a predetermined period of time;

transmitting, on the first computer device, a drug product mapping request to the second computer device and the token;

receiving, on the first computing device, a drug product mapping response and an additional token based on performance of the drug product mapping responsive to the token being valid;

receiving, via the network on the first computing device, associated usage data reflecting a purchaser indication of whether the OTC drug product is for chronic use or acute use;

in response to receipt of the associated usage data reflecting the purchaser indication that the OTC drug product is for chronic use, transmitting, on the first computing device, a drug utilization review (DUR) request and the additional token to the second computing device, the DUR request being a request to perform DUR based on the OTC drug product, the drug product mapping, and patient claims data; and receiving, on the first computing device, a drug interaction alert based on performance of the DUR responsive to the additional token being valid.

9. The method of claim 8, further comprising:
generating an information sharing authorization request; and
receiving an information sharing authorization response in response to generation of the information sharing authorization request.

10. The method of claim 8, wherein the drug product mapping response includes a universal product code (UPC) and a national drug code (NDC) of the OTC drug product.

11. The method of claim 8, wherein the drug interaction alert includes a drug-drug interaction, a drug-disease interaction, or both a drug-drug interaction and a drug-disease interaction.

12. The method of claim 8, wherein the purchase selection data includes a OTC product label scan data.

13. The method of claim 8, wherein the predetermined period of time is approximately 30 minutes.

14. A method comprising:
receiving, from a first computing device, a processing request to a second computing device;

generating, on a second computer device, a token in response to receipt of the processing request, the token being valid for a predetermined period of time;

transmitting, to the first computing device, session authentication packet data in response to receipt of the processing request, the session authentication packet data including the token;

transmitting, via a network the first computing device, associated usage data reflecting a purchaser indication of whether an over-the-counter (OTC) drug product is for chronic use or acute use;

receiving, a drug utilization review (DUR) request and the token from the first computing device;

accessing, on the second computing device, patient claims data based on receipt of the DUR request;

performing, through the second computing device, DUR based on the OTC drug product and the patient claims data; and transmitting, to the first computing device, a drug interaction alert based on performance of the DUR responsive to the token being valid.

15. The method of claim 14, further comprising:
storing usage of the over-the-counter (OTC) drug product by a patient in the patient claims data associated with the patient.

* * * * *